(12) United States Patent
Holbrook

(10) Patent No.: US 7,258,125 B2
(45) Date of Patent: Aug. 21, 2007

(54) SHOPPING CART SANITIZING SYSTEM

(75) Inventor: Rhonda Holbrook, Surprise, AZ (US)

(73) Assignee: RSANECR, Inc., Surprise, AZ (US)

( * ) Notice: Subject to any disclaimer, the term of this patent is extended or adjusted under 35 U.S.C. 154(b) by 363 days.

(21) Appl. No.: 10/817,517

(22) Filed: Apr. 2, 2004

(65) Prior Publication Data

US 2005/0217701 A1  Oct. 6, 2005

(51) Int. Cl.
*B08B 3/00* (2006.01)
(52) U.S. Cl. .................. 134/113; 134/123; 134/129; 134/131
(58) Field of Classification Search .......... 134/113, 134/123, 129, 131, 56 R
See application file for complete search history.

(56) References Cited

U.S. PATENT DOCUMENTS

| | | | | |
|---|---|---|---|---|
| 3,444,867 | A | * | 5/1969 | Thornton ............... 134/123 |
| 3,698,029 | A | * | 10/1972 | Pulliam ................ 15/88.3 |
| 3,854,054 | A | * | 12/1974 | Conn, Jr. ............... 307/41 |
| 4,279,263 | A | | 7/1981 | Pulliam |
| 4,807,319 | A | * | 2/1989 | Poitevin ............... 15/88.3 |
| RE33,849 | E | * | 3/1992 | Detrick ................ 134/123 |
| 6,129,099 | A | * | 10/2000 | Foster et al. ........... 134/57 R |
| 6,260,692 | B1 | | 7/2001 | Sashiede et al. |
| 6,427,707 | B1 | | 8/2002 | Morris |
| 6,439,378 | B1 | | 8/2002 | MacLachlan |
| 6,615,979 | B2 | | 9/2003 | Etherington et al. |
| 6,705,460 | B2 | | 3/2004 | Weiser et al. |
| 2004/0031507 | A1 | | 2/2004 | Ross et al. |
| 2006/0011220 | A1 | * | 1/2006 | Mueller ................ 134/45 |

OTHER PUBLICATIONS www.louisville.com/voicedisplay.html?article=8190, *Clean Machine: Crum's Sani-Dryer invention cleans, disinfects shopping carts; device at east End Winn-Dixie is first in Kentucky*, Leigh Harrington, Voice Tribune, Jan. 23, 2001.
www.cleanshopper.com/transcript-inside-edition.html, *University Expert: Carts Can Be Dirtier Than Public Bathrooms*, Dr. Kelly Reynolds, Original Airdate: Friday, Nov. 14, 2003*.
www.geniusbabies.com/clean-shopper-shopping-cart-cover.html, *Clean Shopper—Keep grocery cart germs away!* *.

* cited by examiner

*Primary Examiner*—Michael Barr
*Assistant Examiner*—Saeed Chaudhry
(74) *Attorney, Agent, or Firm*—Snell & Wilmer L.L.P.

(57) ABSTRACT

The present invention comprises a system and method for removing contaminates from the surface of a shopping cart such as a grocery cart. The system includes subjecting the cart to multiple stages of disinfection, including washing, sanitizing, and drying stages. A shopping cart is subjected to these stages by conveying the cart on a conveyor system past a plurality of nozzles, which are configured to provide a disinfecting fluid such as water, sanitizer or air.

The invention uses sensors to detect the location of a shopping cart during the sanitizing process. The sensors provide indications of the cart's location which may be used to control the operation of the disinfecting stages on the conveyor belt.

13 Claims, 5 Drawing Sheets

SHOPPING CART SANITIZING SYSTEM

FIELD OF INVENTION

The present invention generally relates to grocery carts. More particularly, the invention relates to a system and method for sanitizing grocery carts at a merchant location.

BACKGROUND OF THE INVENTION

The average shopper often uses grocery carts in stores to transport items the shopper wishes to purchase. In the typical scenario, a shopper may place household items, produce, or meat products into the cart for conveying the items to a counter for purchase. The shopper may then remove the items from the cart for purchase. The cart may then be left at the store location for use by subsequent shoppers, who may also use the cart to transport items as described above.

In this way, a typical grocery cart may be used multiple times in a single day by a plurality of shoppers. In some instances, the items placed in the cart may leave an infectious residue, such as blood, mucus, urine, saliva, chemicals, pesticides or the like, on the cart's surface or in the cart's basket. The residue is often left on the cart during each use, thereby causing the residue to build up over time.

Occasionally, a shopper may have an illness which may be easily communicated to other shoppers. For example, a shopper may have the flu or common cold. The germs associated with the illness may be transferred from the shopper to the grocery cart during normal cart usage. As such, when a subsequent shopper uses the cart, the germs may be transferred to the subsequent shopper, thereby passing on the illness as well.

The germs and residue discussed above are called contaminants. Typically, a grocery cart may be in use for many years without the contaminants being removed. A study done by the University of Arizona Microbiology Department tested areas of grocery carts which are most often contacted by the shopper. The test involved testing swabs samples retrieved from the grocery cart for the presence of various kinds of organic matter. The results of the study suggested that a full fifty-four percent of the shopping carts contained harmful contaminants. As such, a need exists for a system and method for protecting the average shopper from the health danger associated with using grocery carts during their shopping experience.

One such system which is used is the Clean Shopper® baby/toddler grocery cart seat cover sold by Babe Ease, LLC of Pelham, N.H. The Clean Shopper cover is a cotton, quilted grocery cart cover that fits over the entire front portion of the grocery cart which is ordinarily used to seat an infant or small child. In this way, a toddler may be seated in the grocery cart without being exposed to the cart's contaminated surface.

One drawback to the Clean Shopper cover is that the cotton or quilted material from which it is constructed is porous. As such, the Clean Shopper cover is prone to having the contaminants transferred to the Clean Shopper cover from the cart's surface during each use, thereby contaminating the Clean Shopper cover. Another drawback is that the Clean Shopper cover does not cover the entire shopping cart. Thus, the contaminates which are present in the cart's basket, for example, may be transferred to the items transported on the basket's surface.

Other systems which are used to protect a shopper from contaminants focus on removal of the contaminants from the carts surface. Typical cart washing systems are like those disclosed in U.S. Pat. No. 6,427,707, entitled "Mobile Super Market Trolley Washer", issued Aug. 6, 2002 to Morris, U.S. Pat. No. 3,444,867, entitled "Mobile Cart Washer", issued Sep. 11, 1967 to Thornton, U.S. Pat. No. 4,279,263, entitled "Cleaning Apparatus", issued Jul. 21, 1981 to Pulliam, U.S. Pat. No. 4,807,319 entitled "Self Contained High Pressure Hot Water Cleaning System for Grocery Carts", issued Feb. 28, 1989 to Poitevin. These cart cleaning systems variously provide an enclosure fitted with cleaning nozzles which emit a washing fluid, sometimes at high pressure and high temperature. However, the systems are not effective for harmful contaminates which may remain on the surface of a cart after the cart is washed.

Consequently, a need exists for a system and method which protects the shopper from contaminates which may exist on any portion of a grocery cart's surface after the cart is subjected to washing.

SUMMARY OF THE INVENTION

The present invention relates to a system and method for sanitizing grocery carts to remove infectious germs, fluids, bacteria, pathogens, or other similar organisms, which are likely to affect the health of a merchant's customer. Particularly, the invention comprises a sanitizing system which cleans, disinfects, and dries the grocery cart between use. The system includes a housing having an entrance for accepting a grocery cart therein, and an exit for exiting the grocery cart once the cart is disinfected. The housing may include an enclosure through which grocery carts may travel. A plurality of system nozzles may be positioned at various locations within the enclosure so as to be directed at the traversing grocery cart, for delivering to the cart a washing, drying or sanitizing fluid.

Grocery carts, which traverse through the enclosure may be subjected to disinfection in stages. For example, a first set of a plurality of nozzles may be configured to wash a cart traversing through the wash stage of the system. A first set of nozzles, for example, may be configured to provide a stream of washing fluid, such as, water alone, or water and detergent or solvent, or the like. The detergent or solvent may be any solid or liquid agent which substantially removes particulates on the cart's surface. Suitable detergents may additionally disinfect the cart's surface or remove the organic particulates affixed thereto. Suitagble detergents may include a bacteriostatic enzymatic detergent, chlorine releasing agent, bactericidal detergent, industrial methylated sprit (70%), glutaraldehyde (2%), aqueous phenolic, or the like. The washing stage may further employ a set of nozzles for rinsing any residual washing fluid from the grocery cart's surface.

At a second stage, the washed grocery cart may be sanitized or disinfected. For example, a second set of nozzles may be configured to provide a disinfecting agent to the grocery cart's surface. The disinfecting agent may be such that the agent will substantially neutralize or remove harmful contaminates remaining on the surface of the cart following the first stage. Preferably, the disinfecting agent is one which disinfects in accordance with the ambient temperature or the temperature of the cart. Suitable disinfecting agents may include citric acid, acetic acid (2%), sulphamic acid, potassium monopersulfate (21%) or the like. Most preferably, the disinfecting agent may work with the stage one fluid to further disinfect the cart surface. The disinfecting stage may further employ a set of nozzles for rinsing any residual washing fluid from the grocery cart's surface.

At a third stage, the grocery cart may be further rinsed to remove the sanitizing agent and then dried to permit the grocery cart to be put back into use. The third stage may include separate sets of nozzles for rinsing and drying. The third stage nozzles may emit an agent for assisting in the drying of the carts surface. Suitable agents include potassium carbonate, calcium chloride, sulfate, an alumina, a silica, molecular sieve, aluminum oxide, or any other agent which substantially removes the moisture from the cart's surface.

The carts may be disinfected individually or when in a stacked formation. That is, the traversing of the grocery cart through the disinfecting enclosure may include a driving apparatus, may be configured to ensure that the grocery cart may traverse through the enclosure permitting the grocery cart to be pushed, pulled or carried through the disinfection stages. Once the cart or stack of carts is sanitized, the cart may by delivered at or through the exit of the enclosure, for subsequent use.

In an exemplary method according to the present invention, a soiled grocery cart is provided to the enclosure entrance, and the sanitizing system is activated. The grocery cart is then provided to the driving apparatus, which motivates the cart through the enclosure, thereby subjecting the grocery cart to the predetermined stages of disinfection. In an exemplary method, the grocery cart may be washed, rinsed, disinfected, rinsed, and dried before the driving means delivers the grocery cart to the enclosure exit.

In the manner described above, the present invention provides a system for sanitizing a grocery cart, which is not found in the prior art.

Additional features and advantages of the present invention are described in, and will be apparent from, the detailed description of the present exemplary embodiments and from the drawings.

BRIEF DESCRIPTION OF THE DRAWINGS

A more complete understanding of the present invention may be derived by referring to the detailed description and claims when considered in connection with the Figures, where like reference numbers refer to similar elements throughout the Figures, and:

DETAILED DESCRIPTION

The present invention addresses the shortcomings of the prior art by providing a grocery cart sanitizing system which removes substantially all of the pathogens, infectious fluids, and other substances which may be harmful to a user. The harmful materials, which may be found on the grocery cart, are typically transferred to the cart through normal use. For example, the materials may be mucus, bodily fluids, dirt, soot, pesticides, blood from meat or poultry products, pathogens transferred from a previous grocery cart user or the like. The invention according to exemplary embodiments described herein is configured to remove those harmful materials by subjecting the grocery cart to a sanitizing system described below.

The present invention may be described herein in terms of functional block components, optional selections and various processing steps. Such functional blocks may be realized by any number of hardware and/or software components configured to perform to specified functions. For example, the present invention may employ various integrated circuit components (e.g., memory elements, processing elements, logic elements, look-up tables, and the like), which may carry out a variety of functions under the control of one or more microprocessors or other control devices. Similarly, the software elements of the present invention, where included, may be implemented with any programming or scripting language such as C, C++, Java, COBOL, assembler, PERL, or the like, with the various algorithms being implemented with any combination of data structures, objects, processes, routines or other programming elements. Further, it should be noted that the present invention may employ any number of conventional techniques for data transmission, signaling, data processing, network control, and the like.

Where required, the system user may interact with the system via any input device such as, a keypad, keyboard, control panel, mouse, personal digital assistant, handheld computer (e.g., Palm Pilot®, Blueberry® device), cellular phone and/or the like). Similarly, the invention could be used in conjunction with any type of personal computer, network computer, work station, minicomputer, mainframe, or the like, running any operating system such as any version of Windows, Windows NT, Windows 2000, Windows 98, Windows 95, MacOS, OS/2, BeOS, Linux, UNIX, Solaris, or the like, by interfacing the control panel, described below, with, for example, a conventional user computer. One skilled in the art will understand the modifications necessary to include the aforementioned systems in the present invention. In that regard, the modifications are considered within the scope of the present invention.

Figure 1:
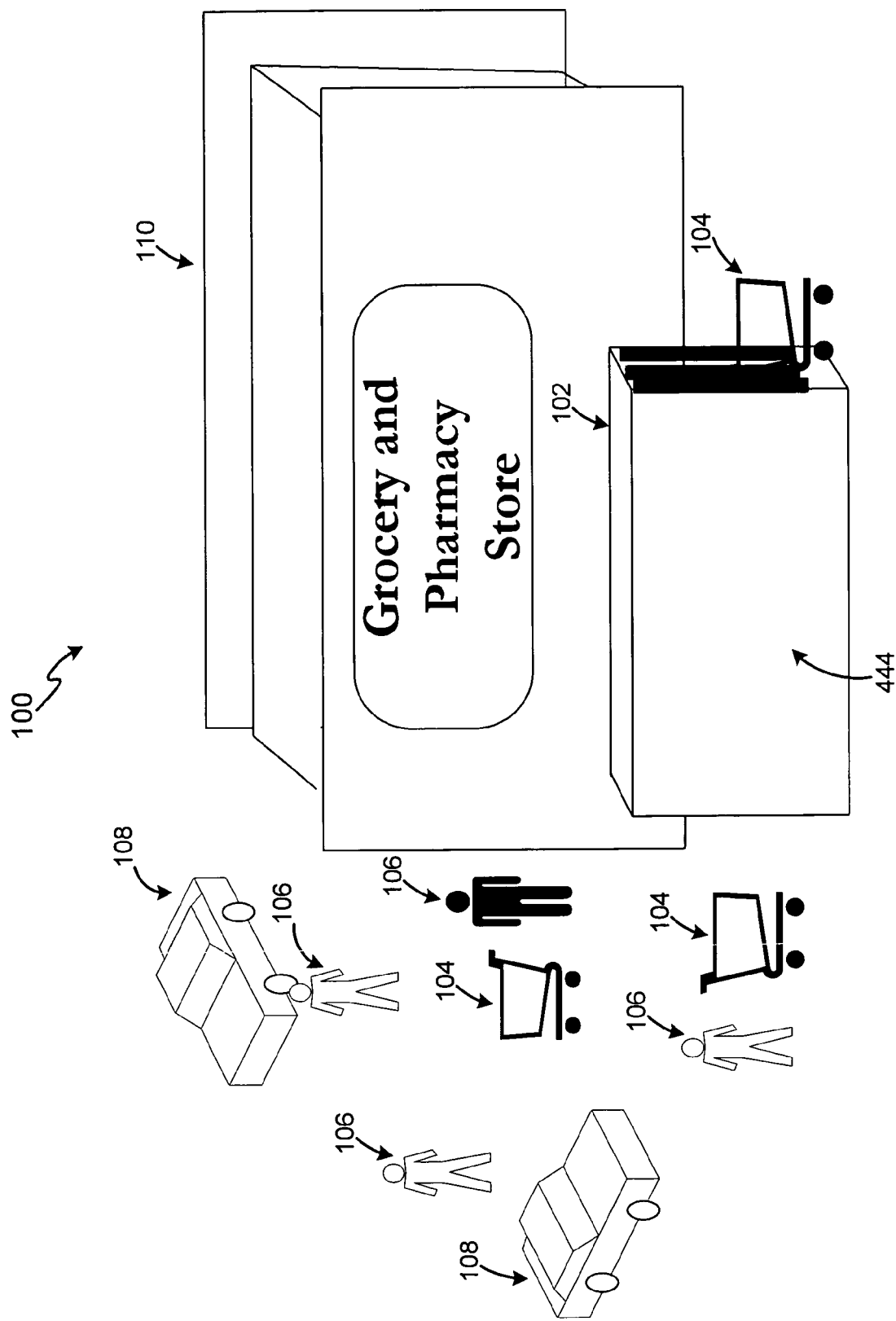
FIG. 1 illustrates an exemplary grocery store environment in which exemplary embodiments of the present invention may be used.
Figure 2:
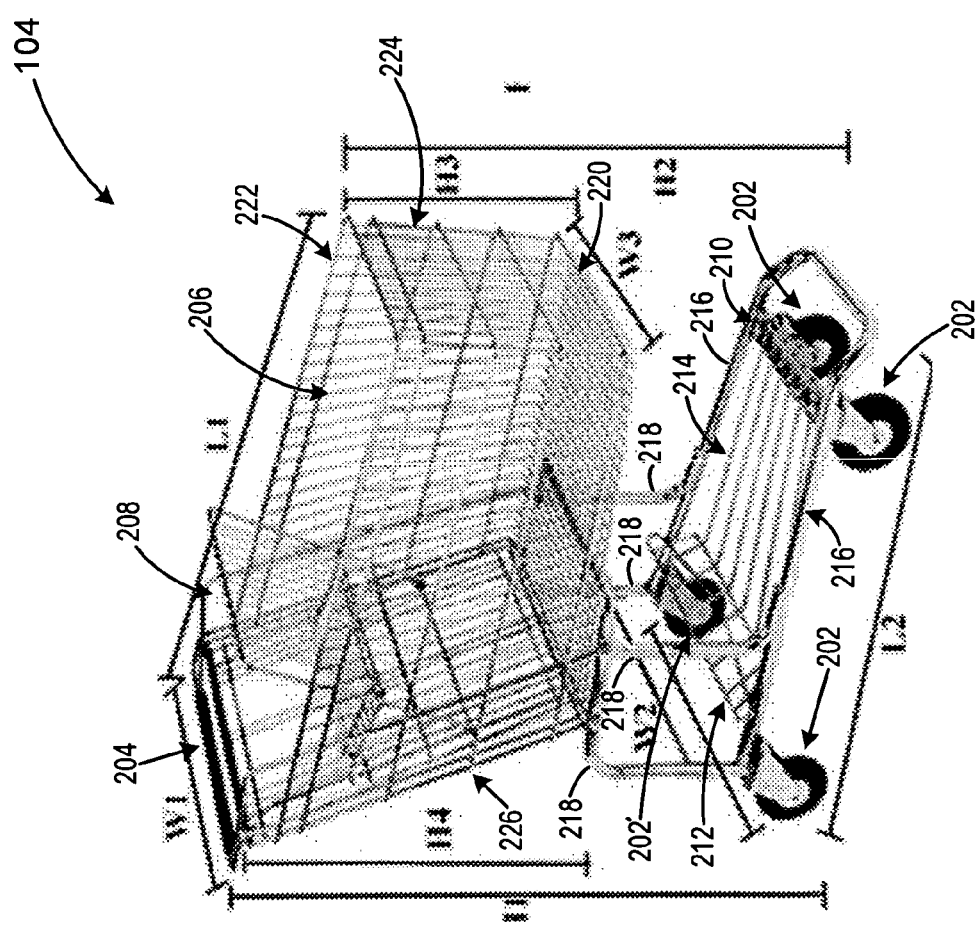
FIG. 2 illustrates an exemplary grocery cart which may be used in accordance with exemplary embodiments of the present invention.

FIG. 1 illustrates a typical grocery store environment 100 in which the present grocery cart sanitizing system and method may be used. Generally, the environment may include a grocery store 110 where a grocery cart user 106 may shop to buy food or household products. Under a typical cart usage scenario during which a grocery cart 104 becomes contaminated, a customer 106 may enter a store 110 and obtain a grocery cart 104 for use in transporting products to be purchased. The products to be purchased may include any number of items from household chemicals (e.g., cleansers), food products (e.g., juices, packaged meat products), or the like. In some instances the packaging of the chemicals or food products may not be properly sealed, permitting castoffs from the food products (e.g., mucus, fat, blood, etc.) or portions of the chemicals to be spilled onto a surface of the cart 110, on which the product to be purchased is transported. For example, if the product to be purchased is in contact with the grocery cart basket 206, child transport area 208, lower grocery cart shelf 214, or any other surface as is shown in FIG. 2. Once the user 106 has completed his shopping, the user 106 may purchase the products transported in the grocery cart 104. The user 106 may then leave the cart inside the grocery store 110 for use by a subsequent customer, or the user 106 may use the cart 104 to transport the products purchased to his car 108 located in the store parking lot (not shown). In the instance where the cart 104 is used to transport the products purchased into the parking lot area, the cart 104 may additionally be soiled by dirt and debris (e.g., gum, oil, transmission fluid, gasoline, etc.) cast onto the cart 104 from, for example, the parking lot surface. After using the grocery cart 104 in any manner as described above, the grocery cart 104 is typically returned into usage without any attention to the harmful materials adhering to the grocery cart surface.

While the present invention is described with respect to a grocery store 110, the invention is not so limited. The present invention may be used in any merchant environment wherein carts are used to transport items. Particularly, the present invention may be used in any merchant environment wherein the cart may be soiled or contaminated with harmful materials during use. Exemplary merchant environments may include grocery stores, laboratories, floral shops, medical treatment facilities, warehouses, or the like.

FIG. 2 depicts an exemplary grocery cart 104, which may be used with the present invention. A suitable grocery cart may include a plurality of wheels 202 used to facilitate movement of the cart from a first location to a second location. The forward most wheels 202 positioned closest to the front of the cart 104 may be connected one to another using, for example, a forward lower shelf forward bar 210 connected such that the forward most wheels 202 may rotate. The rearward most wheels 202 positioned closest to the rear of the cart 104 may be connected using a least two side lower shelf bars 216, which may additionally be connected to lower shelf forward bar 210. Lower shelf 214 may be configured such that the shelf rests between bars 216 and 210. Additionally, lower shelf 214 may include a rearward bar 212, which may, or may not join the rearward wheels 202 one to the other.

Positioned atop and connected to the lower bars 216, via substantially parallel bars 218 may be a basket 206 for use in transporting the products to be purchased. Basket 206 may be any conventional shape, but is shown in FIG. 2 as a basket having substantially planar shaped sides 222 joined by a rear planar shaped side 226, and a front planar shaped side 224. The basket 206 may additionally include a bottom 220 for resting the products to be purchased thereon, and the basket 206 may taper from the rear side 226 to the front side 224, such that the volume of the basket is less toward the front planar shaped side 224.

Basket 206 may include a child passenger area 208 for use in transporting small children, and a handle 204 for use in directing the movement of the cart 208 by the user 106.

Figure 3:
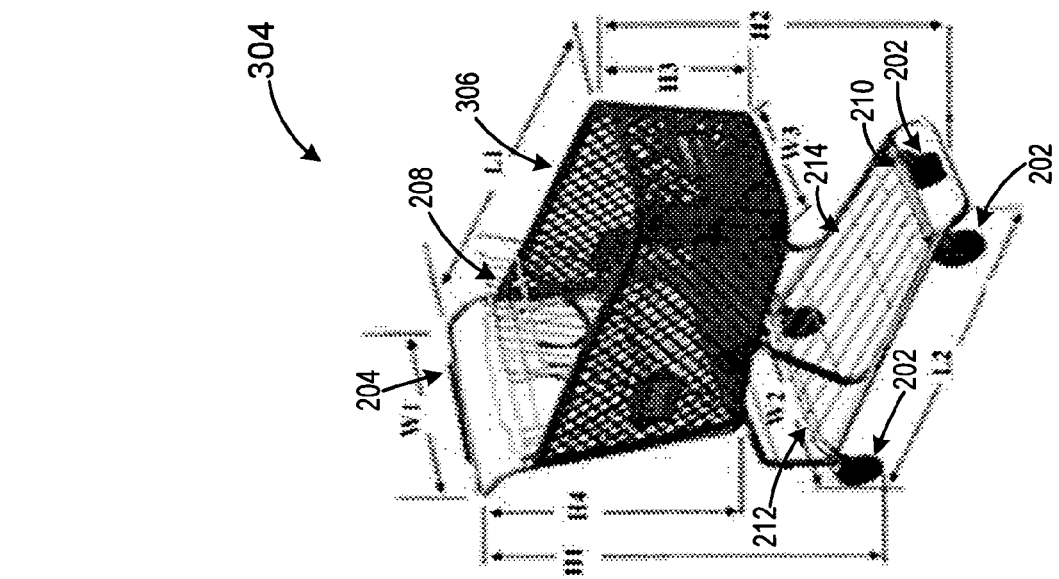
FIG. 3 illustrates another exemplary grocery cart which may be used in accordance with exemplary embodiments of the present invention.

In various conventional constructions of the basket 206, the basket 206 may be made of metal. The basket 206 planar shaped sides 222, 224, 226 and bottom 220 may be made of wire formed in any configuration, such as, for example, a mesh or mesh-like pattern, as shown. Alternatively, the basket, may be constructed of other suitable durable material such as a hardened plastic, as is shown with respect to the cart 304 and basket 306 of FIG. 3.

Cart 104 and 304 may be of any shape, construction or material as is required for its intended use. For example, a cart for use with the invention may be made entirely of metal, as shown in FIG. 2. Alternatively, the cart may be constructed of metal and some there materials such as plastic, rubber, or the like, as is shown with respect to cart 304 of FIG. 3. In another exemplary embodiment, the cart used with this invention may be a flatbed cart as is known in the art. Suitable carts for use with the invention may be manufactured by, for example, Premier Carts, Inc., 3544 West 127th, Terrace, Leawood, Kans. 66209.

As shown in FIG. 1, a grocery cart sanitizing system 102 may be used in disinfecting the carts 104 prior to providing the carts 104 to customers for further use. The sanitizing system 102 may be placed in any location in proximity to the store 110. In one exemplary embodiment, the sanitizing system 102 may be made a part of the store 110, or may be contiguous with the store 102.

Figure 4:
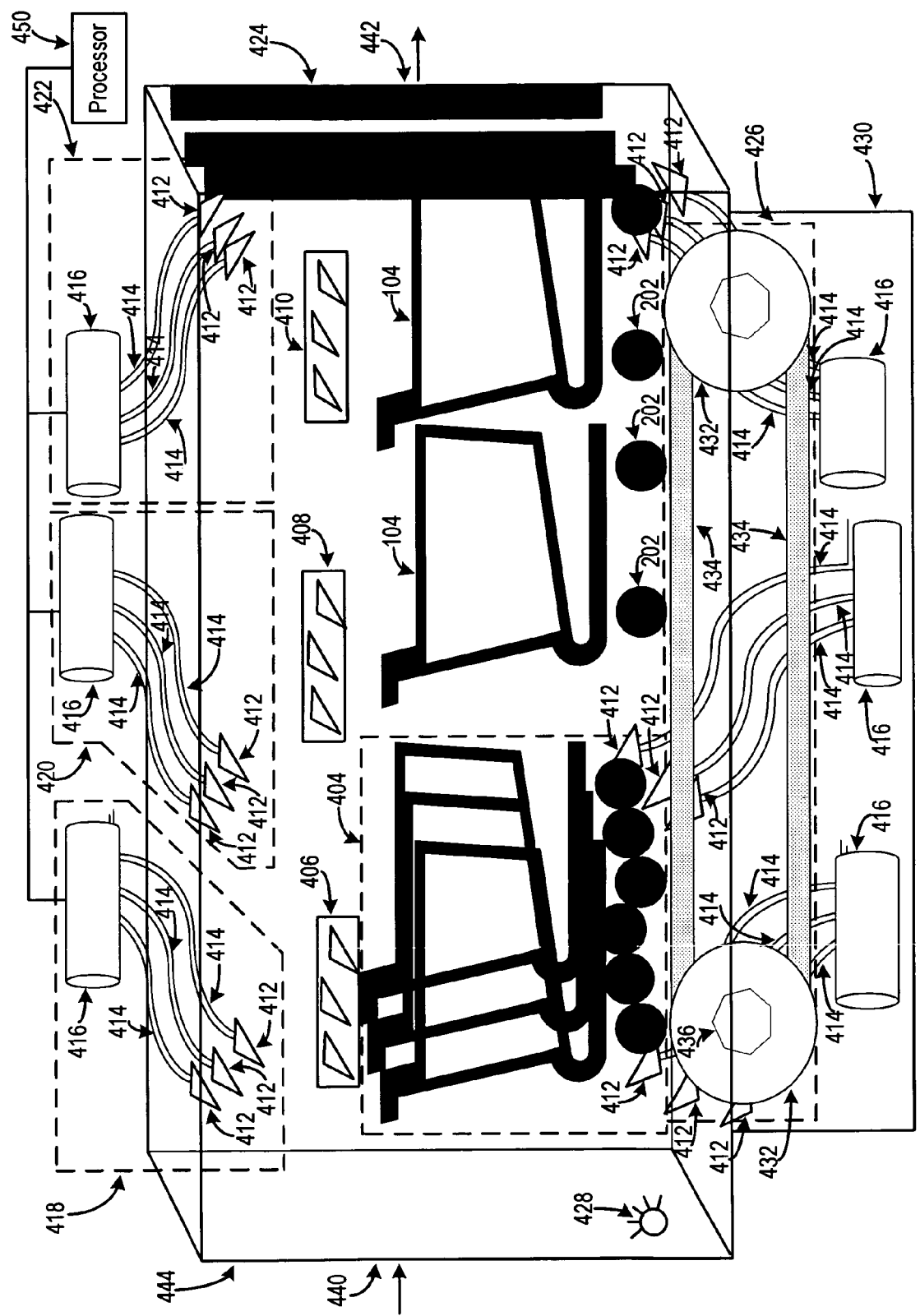
FIG. 4 illustrates an exemplary embodiment of a grocery cart sanitizing system in accordance with the present invention.

As noted, the sanitizing system 102 is configured to disinfect a grocery cart 104 by removing any harmful substances or materials which attach to the cart during normal use. FIG. 4 depicts an exemplary sanitizing system 102 in accordance with an exemplary embodiment of the present invention. As shown, the system 102 includes an enclosure 444 (best seen in FIG. 1). The enclosure 444 may take any shape, although the enclosure is illustrated by way of example to be rectangular. The enclosure 444 may be of sufficient volume to accommodate a grocery cart 104 traversing there through, as well as the accompanying elements described below. With brief reference to FIGS. 2 and 3, the relative heights (H1-H4), widths (W1-W3) and lengths (L1 and L2) of an exemplary grocery cart 104, 304 may be understood with reference to Table 1 shown below.

TABLE 1

Dimensions of Grocery Cart in Inches

| W1 | W2 | W3 | L1 | L2 | H1 | H2 | H3 |
|----|----|----|----|----|----|----|----|
| 18" | 21 7/16" | 13" | 32 7/8" | 27 5/8" | 39" | 31 3/8" | 13 1/4 |

As can be seen in FIG. 4, the system 102 may include a plurality of disinfecting stages 418, 420, 422 configured to wash (stage 418), disinfect (stage 420) and/or dry (stage 422) the cart 104. Each stage may include a set of nozzles 412, which may be connected to a set of irrigation tubes 414, which may further be connected to a fluid delivery source 416. In one exemplary embodiment, the disinfecting stages may additionally be positioned at any location in the enclosure 444, including the enclosure side walls, ceiling or floor. As can be seen in FIG. 1, the The stages may be repeated in the enclosure floor to ensure that the underside of the cart 104 is subjected to the disinfecting process.

The irrigation tubing 414 may be any conventional irrigation tubing as is commonly known. The nozzles 412 may be of sufficient configuration to deliver the desired fluid to volume of the enclosure 444 for providing the fluid to a surface of the cart 104. In one exemplary embodiment, the nozzles 412 may be any conventional nozzles which may be used for ejecting a fluid (e.g., liquid or air). Nozzles 412 may be comprised of a rust resistant metal, such as, for example, copper, or the nozzles 412 may be treated with a rust resistant compound. The nozzles 412 may include an entrance opening for accepting a fluid at a first velocity and an exit opening for emitting or ejecting the fluid of a higher velocity. The nozzles 412 may be adjustable in spray volume, pattern, direction and/or droplet size. For example, the nozzles 412 may be pivotal, such that the fluid emanating therefrom may be directed as desired. Further, the nozzles 412 may be configured to provide multiple fluid ejecting patterns. For example, a user may adjust the nozzles 412 opening to spray in the shape of a cloud wherein the fluid is substantially completely atomized. Alternatively, the nozzles 412 may be adjusted such that less atomization takes place and the fluid droplets are of a larger size providing for a heavier mist or a stream of fluid. Further, a user may adjust the nozzles 412 to emit the fluid in a cloud, cone, stream or other shape. Where the nozzles 412 are used in a drying stage (e.g., stage 422) the opening in the nozzles 412 may be of sufficient size to provide a drying fluid, such as, air at a sufficient velocity to substantially remove all moisture from the grocery cart 104 surface.

It should be noted that to achieve proper dispersion of the fluid from nozzles 412, an appropriate level of fluid pressure must be ordinarily maintained inside of irrigation tubing 414. As such, alternate embodiments of the delivery source 416 described herein may include a pressure regulator (not shown). A pressure regulator suitable for the invention may ensure that the liquid pressure is maintained relatively constant in the tubing 414 and/or at the nozzles 412, so as to ensure proper fluid dispersion. The pressure regulator may be an in-line pressure regulator configured to ensure that the fluid pressure in tubing 414 is maintained at a sufficient level to promote desired fluid dispersion from nozzles 412. Preferably, the pressure is maintained at a sufficient level to promote dispersion of the fluid in the desired dispersion pattern. A suitable in-line pressure regulator, which may be used in exemplary embodiments of this invention, is disclosed in U.S. patent application Ser. No. 5,035,260, issued Jul. 30, 1991, to Davey.

Other suitable pressure regulators capable of regulating the fluid pressure in the delivery system 416, thereby promoting dispersion of the fluid from the tubing 414 and/or nozzles 412, may be used. For example, where the delivery source 416 includes a tank for housing the fluid, the tank may include a pressure regulator configured to regulate the pressure at an outlet of a tank (not shown) containing the fluid. The regulator (not shown) may be disposed or fitted in the housing of the tank, wherein the regulator is not in contact with the fluid, but instead regulates the pressure in the tank by, for example, comparing the pressure inside the tank with ambient pressure and adjusting the pressure in the tank accordingly to a predetermined target pressure. Alternatively, the regulator may regulate the output pressure by measuring the pressure in the tank relative to the pressure in the tubing. Suitable exemplary pressure regulators, which may be used in accordance with the above, are disclosed in U.S. Pat. No. 6,186,168 B1, issued Feb. 13, 2001, to Shultz et al., and U.S. Pat. No. 5,595,209, issued Jan. 21, 1997, to Atkinson et al., for example.

In one exemplary embodiment, delivery source 416 includes a pump (not shown) for facilitating the providing of the fluid from the tank to the irrigation tubing 414. The pump may be any suitable pump for pumping a fluid. The pump may preferably include an inlet in communication with the tank, preferably via a hose. In one exemplary embodiment, the pump is electrical and may be powered via alternating or direct current (e.g., battery). Alternatively, the container pump may be pneumatic.

The system 102 may include sets of a plurality of nozzles 406, 408, and 410 which may be positioned in any location in the enclosure 444 as desired. The sets of nozzles 406, 408, and 410 may be positioned in any desired location so as to be configured to eject a fluid into the enclosure 444 volume. As shown, the nozzles 412 may be positioned in a side wall of the enclosure 444, although it is contemplated that the nozzle sets 406, 408, 410 may be positioned in the enclosure 444 ceiling or floor to ensure that the cart 104 is subjected to the disinfecting process on all possible cart 104 surfaces.

In one exemplary embodiment, the nozzle sets 406, 408, and 410 may be organized to coincide with the disinfecting stages 418, 420, and 422. For example, where stage 418 is a washing stage, then nozzle set 406 may be positioned and configured to facilitate the washing of the cart 104. Where stage 420 is a disinfecting stage, then nozzle set 408 may be positioned and configured to participate in the disinfecting of the cart 104. Similarly, where stage 422 is a drying stage, the nozzle set 410 may be configured and positioned to provide a drying fluid to the surface of cart 104.

As noted, a grocery cart 104 traverses through the volume of the enclosure 444 from the enclosure entrance 440 to the enclosure exit 442, illustrated by the arrows in FIG. 4. The cart 104 may traverse through the enclosure 444 singly, or in a stacked cart formation 404. Stacking grocery carts permits a plurality of carts to be simultaneously subjected to any one stage of the disinfecting process. Stacking of grocery carts is well known, and as such, will not be discussed herein in detail.

System 102 may include a driving apparatus 426 for use in traversing the cart 104 through the enclosure 444. The driving apparatus 426 may be any suitable apparatus for ensuring that the cart may move from the enclosure entrance 440 to the enclosure exit 442. In one exemplary embodiment, the driving apparatus may include a conventional conveyor belt 434 which is substantially continuous in that the belt may not have a perceptible endpoint. The conveyor belt 434 may be a stripbelt, roller, freeflow, slat and flexlink, or any suitable belt as is commonly known. The belt 434 may be in contact with a rotary motor 436 for driving the belt in a continuous circular motion. For example, when the motor 436 rotates in a clockwise direction, then the belt will likewise rotate in a clockwise fashion. A suitable drive apparatus which may be used with the present invention is disclosed in U.S. Pat. No. 6,705,460 B2, issued Mar. 16, 2004, to Weiser et al.; U.S. Pat. No. 6,615,979 B2, issued Sep. 9, 2003, to Etherington et al.; U.S. Pat. No. 6,439,378 B1, issued Aug. 27, 2002, to MacLachlan; U.S. Pat. No. 6,260,692 B1, issued Jul. 17, 2001, to Sashide et al., and the like.

In an exemplary embodiment of the drive apparatus 426, a cart 104 may be in physical contact with the belt 434 as the cart 104 traverses through the enclosure 444. The cart wheels 202 may rest on the belt 434 such that a resistive friction is created between the belt 434 and the wheels 202. As the belt rotates, for example, in a clockwise direction, the cart 104 may traverse through the enclosure from the enclosure entrance 440 to the enclosure exit 442. To facilitate the movement of the cart 104, the wheels 202 of the cart 104 may be fixed to prevent rotation. For example, the wheels 202 may be locked using any suitable locking mechanism that is found in the art.

Figure 5:
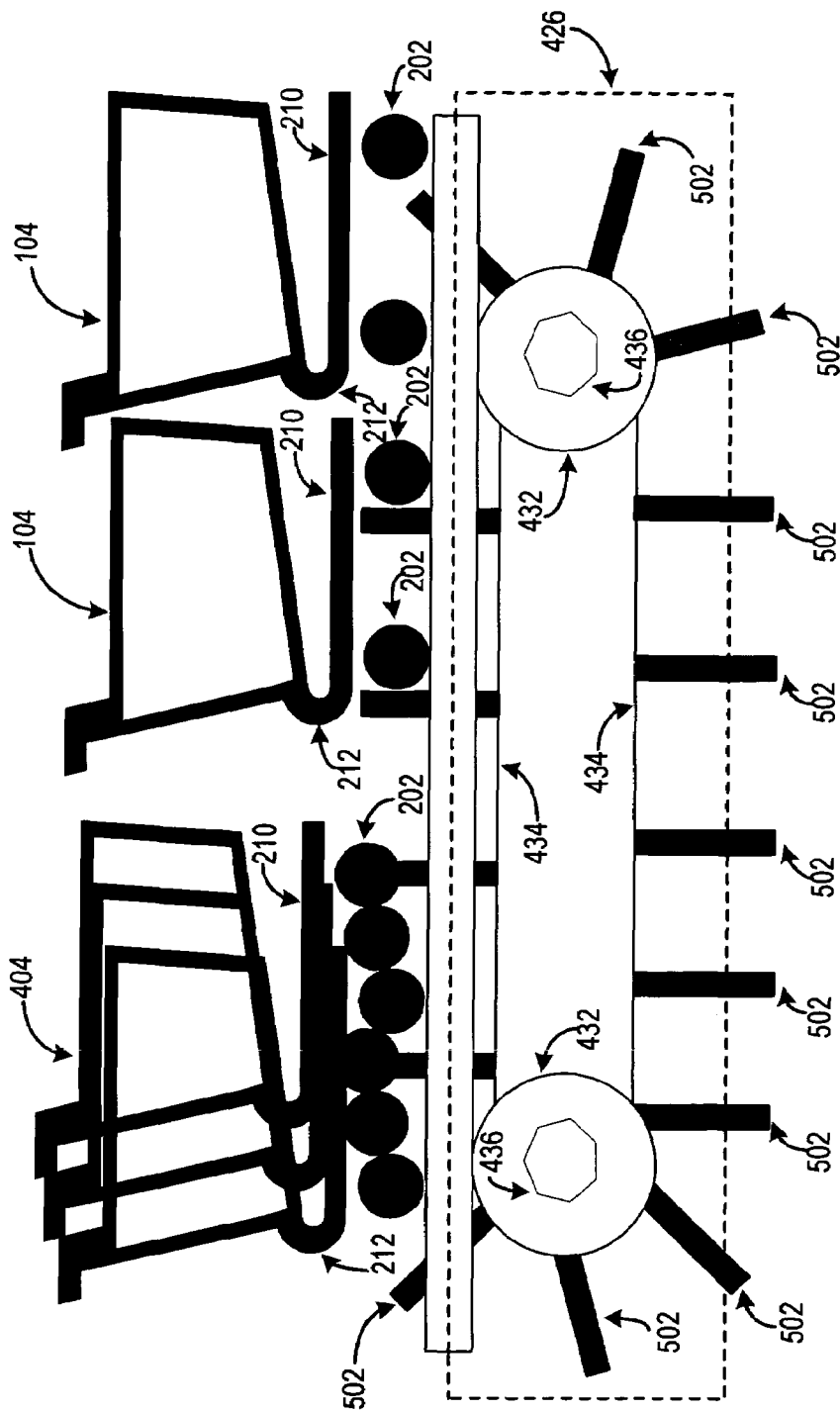
FIG. 5 depicts an alternate embodiment of the driver apparatus in accordance with an exemplary embodiment of the present invention.

FIG. 5 depicts another exemplary embodiment of the drive apparatus 426. In the embodiment shown, the apparatus 426 includes conveyor belt ribs 502 configured to project outwardly from the conveyor belt 434. Preferably, the ribs 502 are of sufficient length to project upwards from the enclosure 444 bottom and most preferably, the ribs 502 are of sufficient length to engage or contact a bottom surface of the cart 104. The ribs 502 may be of sufficient length to engage the rearward bar 212 or the front bar 210 of cart 104. The ribs 502 may be constructed of any rigid material such as metal, hard plastic, a composite, a weaved material or the like. In this manner, the cart 104 may be propelled through the enclosure 444 when the conveyor belt 434 rotates. For example, as the belt 434 rotates clockwise, at least one of the ribs 502 may contact the forward bar 210 of the cart 104 (or stacked carts 404) and move the cart 104 by pushing the bar 210 from entrance 440 to exit 442. Once the cart 104 reaches exit 442, the bar may disengage from the bar 210 and descend into the floor of the enclosure. In addition, the ribs 502 may be spaced such that at least one of the plurality of ribs 502 is contacting a rearward bar 212 or a forward bar 210 of a cart 104, or multiple carts 404, traversing through the enclosure 444 volume.

Figure 6:
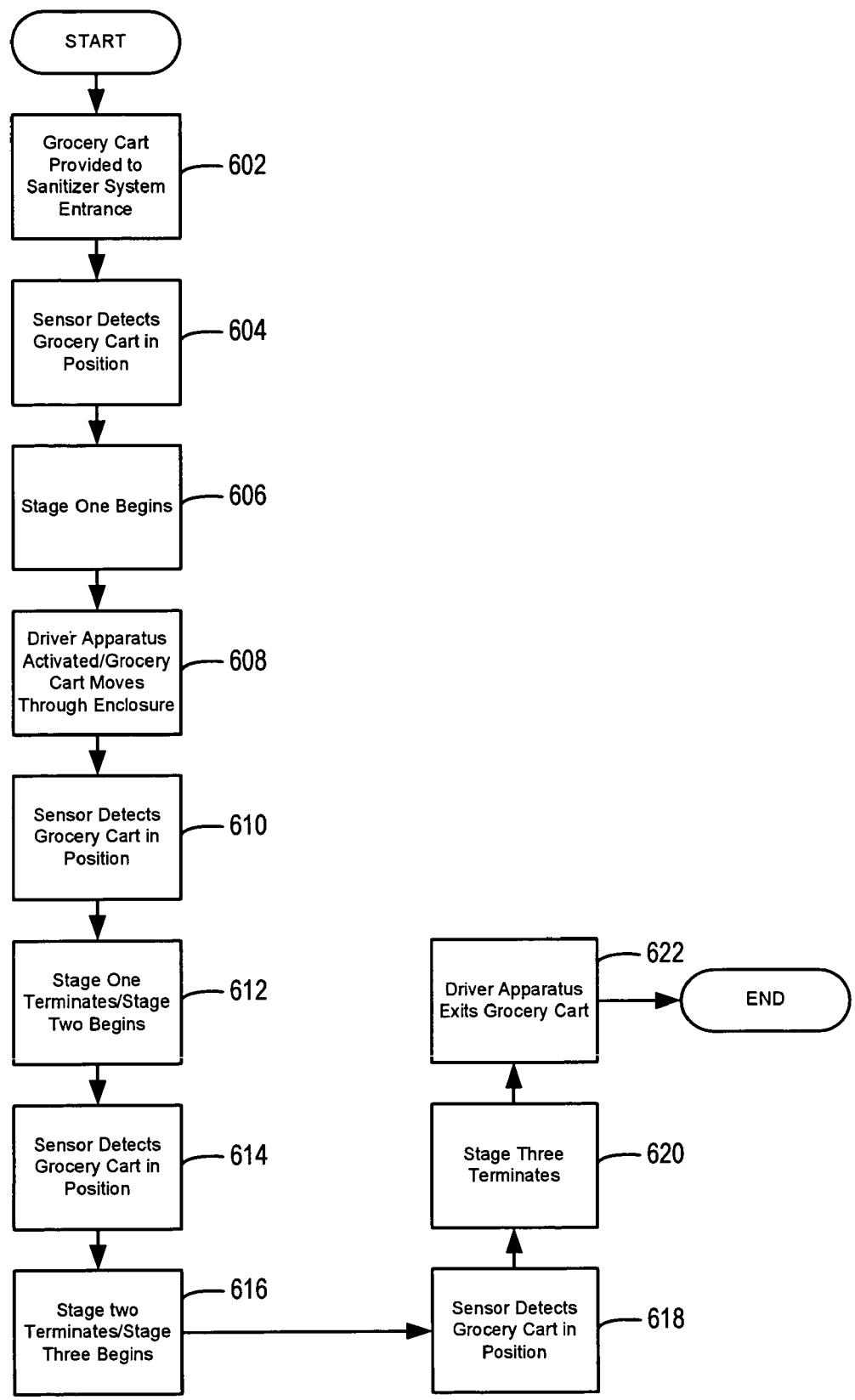
FIG. 6 depicts an exemplary flowchart depicting the operation of an exemplary embodiment of the present invention.

With reference to FIG. 6, and continued reference to FIG. 4, the operation of the system 102 may be understood. The method begins with the cart 104 being presented to the entrance 440 of the enclosure 444 (step 602). In the exemplary method illustrated, the enclosure 444 includes a plurality of sensors 428 which may be used to detect the presence of the cart 104 at the enclosure 444 entrance 440. The enclosure 444 may additionally include a plurality of sensors throughout the enclosure 444 which may be positioned and configured to detect the location of the cart 104 as the cart 104 traverses through the enclosure 444. The sensors 428 may be configured to detect when a cart 104 completes a stage 418, 420, 422 of the disinfecting process and is prepared for the following stage, or for exiting the enclosure 444. As such, the sensors 428 may be in communication with a system processor 450 which may control the operation of the stages 418, 420, 422. The processor 450 may be any suitable computer system for controlling delivery sources 416. For example, the sensors 428 may be in communication with the processor 450 to provide the processor a signal for activating the delivery source 416 pump. The processor 450 may then send a signal to the delivery source 416 pump thereby causing the pump to increase the fluid pressure in the irrigation tubing 414. Once the fluid pressure is increased to the desired level, the fluid may then be ejected from the nozzles 412 and onto a surface of the cart 104 traversing through the enclosure 444. The sensors 428 may be configured and positioned such that the sensors 428 detect when a cart 104 completes a stage 418, 420, 422 of the sanitizing process, and send a signal to the processor 450 to cease operation of a stage 418, 420, 422 and begin the operation of a subsequent stage 418, 420, 422.

Thus, when the cart 104 is detected by a sensor 428 (step 604), a sensor 428 may send a signal to the processor 450 to begin stage one of the sanitizing process (e.g., stage 418) (step 606). A sensor 428 may additionally send a signal to the processor 450 to begin rotation of the belt 434 to traverse the cart 104 through the enclosure 444 volume (step 608). Stage one in this example, may be a washing stage. The delivery source 416 may provide a washing fluid such as water and a detergent or solvent to the cart 104 surface for removing any harmful materials or dirt which may be resting on the cart 104 surface. Stage one may additionally include a rinse cycle for rinsing the washing fluid from the cart 104 surface prior to the cart 104 traversing to the subsequent stages (e.g., stage 420 and 422).

Once the cart has traversed through stage one, a sensor 428 may detect the position of the cart 104 (step 610). A sensor 428 may then send a signal to the processor 450 to cease operation of stage one and begin operation of stage two (step 612). Stage two may be a disinfecting stage. As such, the processor 450 may send a signal to the delivery source 416 for ejecting a disinfecting agent onto the surface of the cart 104 in similar manner as was discussed with respect to the washing fluid. The pressure in the irrigation tubing may be raised to a desired level by a delivery source 416 pump, thereby causing the disinfecting agent to eject from the nozzles 412 onto a surface of the cart 104. The disinfecting agent may be any chemical composition which is designed to neutralize the harmful affects of any contaminate that still exists on the cart after stage one (e.g., the washing stage) is complete. Suitable disinfecting agents are well known, and will not be discussed herein for brevity.

In similar manner as is discussed above, a sensor 428 may detect the position of the cart 104 traversing through the enclosure 444 (step 614). A sensor 428 may then send a signal to the processor 450 to terminate the operation of stage two and begin operation of stage three (step 616). Stage three may be a rinsing/drying stage, wherein the processor 450 sends a signal to the delivery source 416 to provide, a rinsing fluid, such as water, or a drying fluid, such as air, to a surface of the cart 104. Where stage three includes drying the cart 104, the nozzles 412 may be of sufficient size to eject the air at sufficient velocity and spatial area to ensure that substantially all of the moisture on the cart 104 surface is removed. In one exemplary embodiment, the exit of the enclosure 442 may include an air curtain (not shown) affixed to the upper most portion of the exit 442 opening. The air curtain may be any suitable apparatus which produces a wall of air at the exit 442. Suitable air curtains include any suitable conventional air door or air curtain produced by Mars Air Doors of Gardena, Calif. or Berner International Corp of New, Castle Pa., or the like.

Once the cart 104 traverses through stage three (e.g., the drying stage) a sensor 428 may detect the position of the cart 104 (step 618) and send a signal to the processor 450 indicating that the cart 104 has traversed through stage three. The processor 450 may send a signal to the delivery source 416 to terminate the operation of stage three (e.g., stage 422) (step 620). A sensor 428 may then send a signal to the processor that the cart is at the enclosure exit 442 (step 622). The cart 104 may then removed from the enclosure for use by a store 110 customer 106.

In another exemplary embodiment, the exit 442 may include a conventional strip curtain 424 which may be affixed at the upper most portion of exit 442 and made to hang such that the opening provided by the exit 442 is substantially concealed. The curtain 424 may include one or more hanging portions which hang loosely such that a traversing cart 104 may pass therethrough. Additionally, the curtain 424 may be such that the drying agent or fluid emitted from nozzles 412, or the air from the air curtain, is substantially confined to the area containing the cart 104 nearest most the exit 442. The curtain 424 may be constructed of any suitable material such as vinyl, plastic, rubber, fiber, textile, or the like. A suitable strip door may be any conventional strip door produced, for example, by Flexon Co. of Leetsdale, Pa.

It should be noted that the speed at which the belt 434 rotates may be determined by the system 102 user. The belt 434 may rotate at a sufficient speed to permit a cart 104, or stacked carts 404 to traverse through the enclosure 444 volume. Preferably, the speed of the belt 434 is such that the cart 104, or stacked carts 404 traverse in a manner permitting the cart 104 to be subjected to the stages 418, 420, 422, allowing the stages 418, 420, 422 to optimally operate on the cart 104 surface. Thus, the speed of the belt 434 may vary in accordance with the requirements of the particular stage in which the cart 104 is positioned.

The preceding detailed description of exemplary embodiments of the invention makes reference to the accompanying drawings, which show the exemplary embodiment by way of illustration. While these exemplary embodiments are described in sufficient detail to enable those skilled in the art to practice the invention, it should be understood that other embodiments may be realized and that logical and mechanical changes may be made without departing from the spirit and scope of the invention. For example, the enclosure described herein may include a conventional temperature sensor in the event the temperature of the disinfecting stages or the ambient temperature needs to be monitored. The temperature sensor may be in communication with the enclosure processor, which may be in further communication with a heating apparatus. The processor may provide a signal to the heating apparatus to control the temperature of the disinfecting stage agents prior to emitting the agents from the nozzles. Alternatively, the heating apparatus may be included in the enclosure for heating the ambient temperature thereof. Conventional heating apparatuses for may be used with the invention. Thus, the preceding detailed description is presented for purposes of illustration only and not of limitation, and the scope of the invention is defined solely by the appended claims and their legal equivalents when properly read in light of the preceding description. For example, the steps recited in any of the method or process claims may be executed in any order and are not limited to the order presented.

The invention claimed is:

1. A system for sanitizing a shopping cart, comprising:
   a fluid delivery source for providing a fluid;
   a plurality of nozzles for receiving said fluid and ejecting said fluid, said plurality of nozzles being positioned in multiple sets of a plurality of nozzles, where each set the plurality of nozzles is directed to provide said fluid to the centermost area of an enclosure;
   a conveyor belt system for conveying a shopping cart form a first end of the enclosure to a second end of said enclosure, said conveyor belt system comprising a conveyor belt in communication with a conveyor belt motor for use in moving the conveyor belt, said conveyor belt for transporting the shopping cart thereon;
   a plurality of sensors for providing a signal indicative of the position of said shopping cart in said enclosure; and
   a processor controlling said conveyer belt system for receiving said sensor signal and activating said delivery source in accordance with the position of said shopping cart and starting the movement of the conveyer belt based on information received from the sensors.

2. A system according to claim 1, wherein said fluid is at least one of a sanitizing fluid, washing fluid, rinsing fluid and air.

3. A system according to claim 2, wherein said fluid is a disinfecting agent for neutralizing the harmful affects of contaminants.

4. A system according to claim 3, wherein said processor receives said sensor signal and activates said conveyor belt motor in accordance with the position of said shopping cart.

5. A system according to claim 4, wherein said sets of a plurality of nozzles are organized in stages, wherein at least one of said stages is for disinfecting a surface of said shopping cart.

6. A system according to claim 4, wherein said sets of a plurality of nozzles are organized in stages, wherein at least one of said stages is for washing a surface of said shopping cart.

7. A system according to claim 4, wherein said sets of a plurality of nozzles are organized in stages, wherein at least one of said stages is for drying a surface of said shopping cart.

8. A system according to claim 4, wherein said sets of a plurality of nozzles are organized in stages, and wherein each stage comprises a stage fluid delivery source.

9. A system according to claim 8, wherein at least one of said plurality of sensors provides a signal to said processor indicative of the position of said shopping cart in said enclosure, said processor thereby activating the operation of at least one of said stages fluid delivery sources in accordance with said shopping cart position.

10. A system according to claim 9, wherein said at least one of said plurality of sensors provides a signal to said processor indicative of the position of said shopping cart in said enclosure, said processor providing a signal to said motor for operating said conveyer belt in accordance with said shopping cart position.

11. A system according to claim 1, wherein said conveyor belt further includes radially positioned ribs, said ribs being of a sufficient length to contact said shopping cart in said enclosure, said ribs being comprised of a rigid material.

12. A system according to claim 1, further including a heating apparatus for heating said fluid.

13. A system according to claim 1, further including a heating apparatus for heating the ambient temperature of said enclosure.

* * * * *